US011872028B2

(12) United States Patent
Kandori et al.

(10) Patent No.: US 11,872,028 B2
(45) Date of Patent: Jan. 16, 2024

(54) BIOLOGICAL MEASUREMENT METHOD

(71) Applicant: HITACHI, LTD., Tokyo (JP)

(72) Inventors: Akihiko Kandori, Tokyo (JP); Ryuzo Kawabata, Tokyo (JP); Kuniomi Ogata, Tokyo (JP); Takako Mizoguchi, Tokyo (JP); Tsukasa Funane, Tokyo (JP)

(73) Assignee: HITACHI, LTD, Tokyo (JP)

(*) Notice: Subject to any disclaimer, the term of this patent is extended or adjusted under 35 U.S.C. 154(b) by 777 days.

(21) Appl. No.: 16/988,176

(22) Filed: Aug. 7, 2020

(65) Prior Publication Data
US 2021/0076978 A1 Mar. 18, 2021

(30) Foreign Application Priority Data

Sep. 12, 2019 (JP) .................................. 2019-166438

(51) Int. Cl.
*A61B 5/08* (2006.01)
*A61B 5/282* (2021.01)
(52) U.S. Cl.
CPC ............ *A61B 5/0809* (2013.01); *A61B 5/282* (2021.01); *A61B 2562/0223* (2013.01)
(58) Field of Classification Search
CPC .................. A61B 5/0809; A61B 5/282; A61B 2562/0223
See application file for complete search history.

(56) References Cited

U.S. PATENT DOCUMENTS

| 5,421,345 A * | 6/1995 | Lekholm .............. A61B 5/0535 600/506 |
| 2001/0009975 A1* | 7/2001 | Tsukada ............. G01R 33/0354 600/409 |
| 2003/0016010 A1 | 1/2003 | Kandori et al. |
| 2004/0210127 A1* | 10/2004 | Kandori ................. A61B 5/243 600/409 |
| 2012/0157866 A1 | 6/2012 | Ross et al. |

(Continued)

FOREIGN PATENT DOCUMENTS

| JP | 2002-243766 A | 8/2002 |
| JP | 2003-035758 A | 2/2003 |
| JP | 2016-059625 A | 4/2016 |

OTHER PUBLICATIONS

Akihiko Kandori, "Two-Dimensional Mapping of Impedance Magnetocardiograms", Jul. 2002, IEEE Transactions on Biomedical Engineering, pp. 721-728 (Year: 2002).*

(Continued)

*Primary Examiner* — Adam Z Minchella
(74) *Attorney, Agent, or Firm* — Volpe Koenig

(57) ABSTRACT

To perform respiratory monitoring and cardiac-output measurement on general patients, an aspect of a biological measurement apparatus includes: at least two electrodes that are attached to a living body; a power supply that causes an AC current to flow between the two electrodes; at least two coils that are placed so as to sandwich a line linking the two electrodes, and detect a magnetic field related to a change in the AC current accompanying a change in impedance of the living body; and a detection circuit that performs addition or subtraction of signals related to the magnetic field detected with the two coils, and outputs the signals as a change in the impedance.

13 Claims, 8 Drawing Sheets

(56) References Cited

U.S. PATENT DOCUMENTS

2018/0143150 A1* 5/2018 Bezemer ............. A61B 5/4875
2019/0133478 A1* 5/2019 Varcoe ................. A61B 5/245

OTHER PUBLICATIONS

Japanese Office Action dated Nov. 1, 2022 for Japanese Patent Application No. 2019-166438.
Yamamori, Shinji "The Latest Trend of Sensors for Respiratory Monitoring," The Japanese Journal of Medical Instrumentation, vol. 80, No. 1, (2010) (with English translation of "3. Respiratory monitoring method 2) Chest/belly movement detection").

* cited by examiner

BIOLOGICAL MEASUREMENT METHOD

BACKGROUND OF THE INVENTION

1. Field of the Invention

The present invention relates to biometric technologies.

2. Description of the Related Art

As monitoring methods to be applied to bedside monitors for patients or respiratory monitors essential for rehabilitation, three methods, that is, the method of detecting respiration-related gases, the method of detecting respiratory air flows, and the method of detecting chest and abdomen motions in breathing have been practically used. The most precise indexes of respiratory monitoring include arterial blood oxygen partial pressure ($PaO_2$) and arterial blood carbon dioxide partial pressure ($PaCO_2$), which are indexes related to blood gases. These are measured by blood flow gas analyzers, but the measurement requires collection of blood, and is difficult to perform consecutively.

In addition, regarding the method of detecting respiratory air flows, the only method of accurately monitoring ventilatory volumes is the use of flow sensors. However, although flow sensors are used for patients with serious illness like those who are unconscious and intubated, flow sensors are not used for patients who can make motions as well as respiratory motions since the precision deteriorates significantly due to physical motions, talking and the like.

On the other hand, as one of methods in which the most studies have been progressed, there is impedance plethysmography (hereinafter, chest impedance method). In the chest impedance method, an AC current is caused to flow through a living body, and a change in electric impedance that occurs at that time is detected. The respiratory monitoring performed by using the chest impedance method is described in "The Latest Trend of Sensors for Respiratory Monitoring," The Japanese journal of medical instrumentation, Vol 80, No. 1, (2010) Shinji Yamamori.

While "The Latest Trend of Sensors for Respiratory Monitoring," The Japanese journal of medical instrumentation, Vol 80, No. 1, (2010) Shinji Yamamori described above discloses respiratory monitoring performed by using the chest impedance method, it describes problems and one of them is that the method is susceptible to the influence of physical motions. In a case where respiratory monitoring is performed by the chest impedance method on patients who are in general wards or receiving in-home care, and can talk or move their bodies (hereinafter, general patients), the influence of physical motions becomes a problem.

Although, according to studies, respiratory monitoring performed by the chest impedance method enables accurately measurement of ventilatory volumes and the like, respiratory monitoring performed by the chest impedance method is significantly influenced by physical motions or electrocardiographs in reality, so is not used in clinical settings.

In view of this, an object of the present invention is to provide a biological measurement apparatus capable of performing respiratory monitoring and cardiac-output measurement on general patients.

SUMMARY OF THE INVENTION

In order to achieve the object described above, one aspect of a biological measurement apparatus of the present invention includes: at least two electrodes that are attached to a living body; a power supply that causes an AC current to flow between the two electrodes; at least two coils that are placed so as to sandwich a line linking the two electrodes, and detect a magnetic field related to a change in the AC current, the change accompanying a change in impedance of the living body; and a detection circuit that performs addition or subtraction of signals related to the magnetic field detected with the two coils, and outputs the signals as a change in the impedance.

According to the present invention, it is possible to perform respiratory monitoring and cardiac-output measurement on general patients.

DESCRIPTION OF THE PREFERRED EMBODIMENTS

In the following explanation, identification numbers are used as identification information of various objects, but identification information on types other than identification numbers (e.g. identifiers including alphabetical characters or symbols) may be employed.

In addition, in the following explanation, in a case where elements of the same types are explained while being not distinguished from each other, reference symbols (or common symbols of the reference symbols) are used, and in a case where elements of the same types are explained while being distinguished from each other, identification numbers (or reference symbols) of the elements are used, in some cases.

First Embodiment

Hereinafter, a first embodiment is explained with reference to the drawings.

Figure 1:
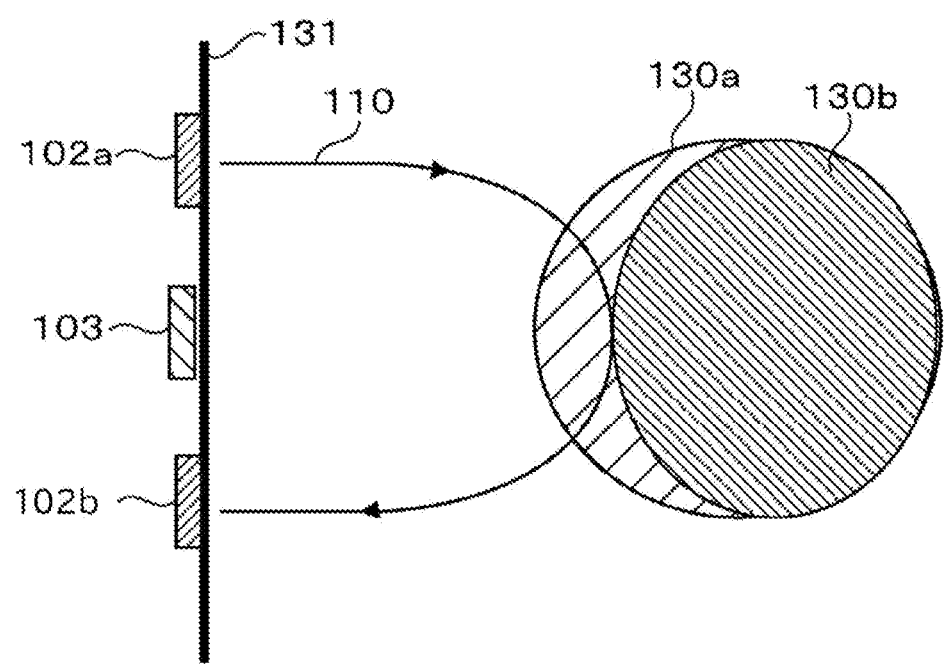
FIG. 1 is a figure for explaining the principle of respiratory monitoring of a biological measurement apparatus according to an embodiment.

FIG. 1 is a figure for explaining the principle of respiratory monitoring of a biological measurement apparatus according to an embodiment.

When a high-frequency micro current (hereinafter, current) 110 is caused to flow through a living body by using two electrodes 102a and 102b pasted onto the chest, voltage drop occurs in accordance with an electrical characteristic unique to tissue of the living body. Here, in the living-body tissue through which the current is caused to flow, when there is a substance whose electrical characteristics are significantly different from those of other tissue of the living body such as blood or intrapulmonary air, if a change in the amount of the substance or the like occurs along with a heartbeat or breathing, the change is observed as a change in the impedance of the living-body tissue through which the current is caused to flow. In respiratory monitoring in a first embodiment and a second embodiment, changes in the amount of current generated from such changes in the impedance are presumably proportional to changes in blood or intrapulmonary air, and magnetic-field changes generated from those changes in current are measured.

131 represents a thoracic wall, and a body having lungs and a diaphragm 130 thereinside is present on the right side of the thoracic wall 131. The lungs 130 expand at the time of inhalation accompanying breathing (the diaphragm contracts and lowers) to be a state illustrated by 130a, and shrink at the time of expiration (the diaphragm relaxes and rises) to be a state illustrated by 130b.

When the current 110 is caused to flow through a subject by the two electrodes 102a and 102b, a change occurs in the intrapulmonary air due to expansion or shrinkage of the lungs and the diaphragm, the path of the current 110 changes, and thereby the impedance detected by a magnetic sensor or coils 103 changes. It should be noted however that the total impedance between the two electrodes 102a and 102b is susceptible to the influence of physical motions.

In the first embodiment, a biological measurement apparatus capable of respiratory monitoring that is less affected by physical motions is explained.

Figure 2:
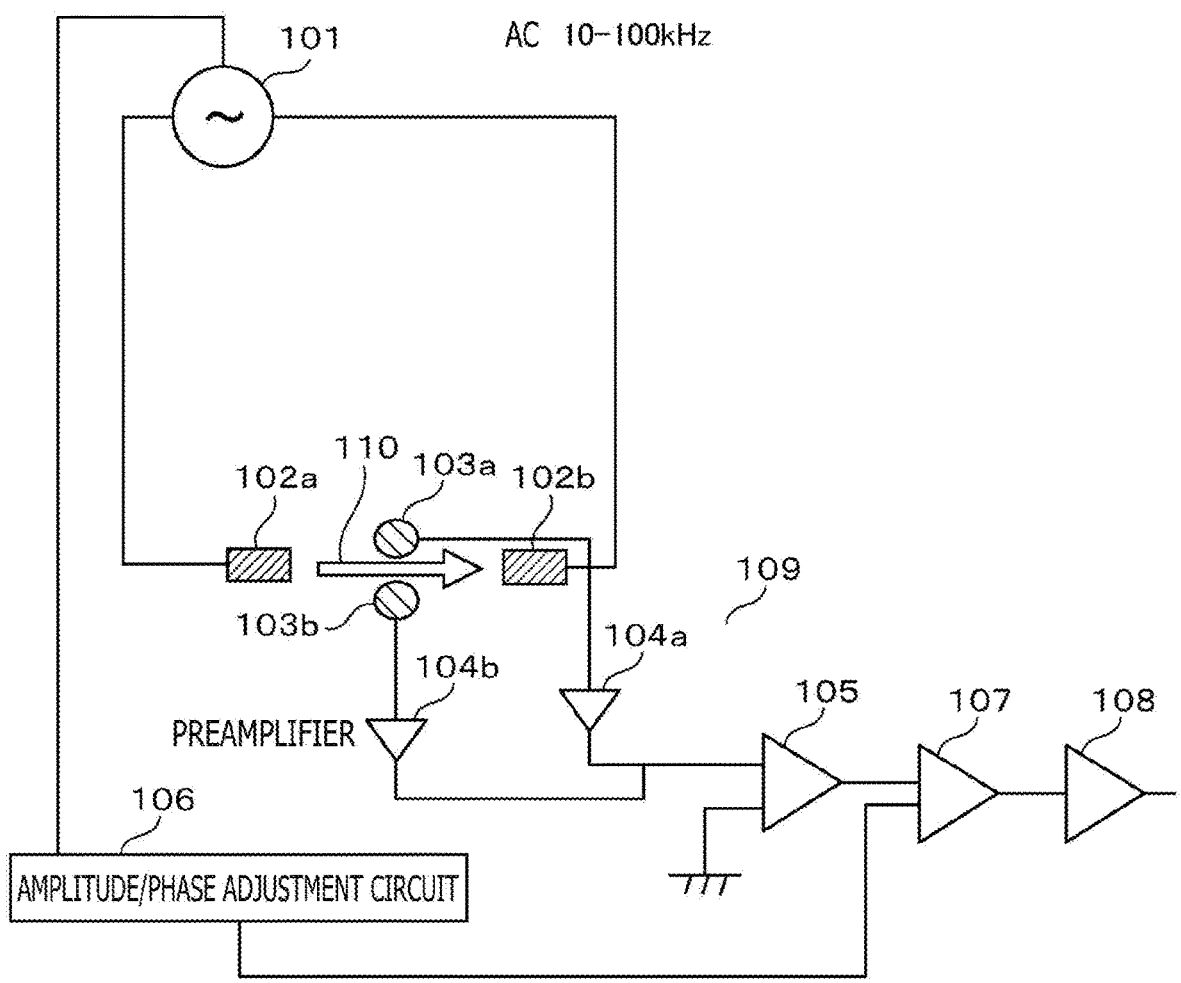
FIG. 2 is a figure illustrating the overview of a biological measurement apparatus according to a first embodiment.

FIG. 2 is a figure illustrating the overview of a biological measurement apparatus according to the first embodiment.

The micro current 110 is caused to flow through the inside of the body by the two electrodes 102a and 102b connected to an AC power supply 101. The AC power supply 101 generates a frequency of 10 to 100 kHz, and a current up to 10 mA. Changes in the path of the current generated by the two electrodes 102a and 102b are detected as changes in the impedance based on voltages detected at two coils 103a and 103b. As the two electrodes 102a and 102b, electrodes of an electrocardiograph can be used.

The voltage detected by the coil 103a is amplified by a preamplifier 104a, and the voltage detected by the coil 103b is amplified by a preamplifier 104b. An adder 105 performs addition or subtraction of signals obtained through the amplification at the preamplifiers 104a and 104b.

Figure 3:
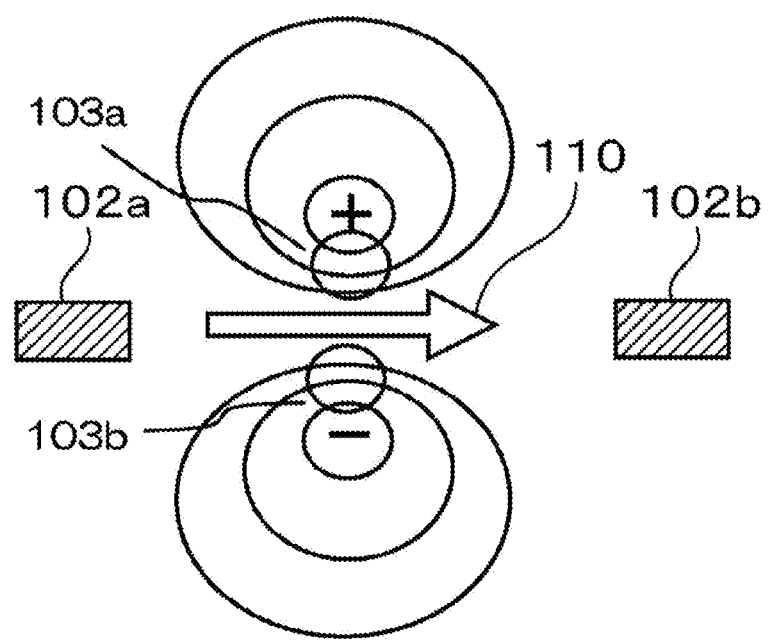
FIG. 3 is a figure illustrating a magnetic-field distribution generated between electrodes of the biological measurement apparatus of the first embodiment.

As illustrated in FIG. 3, when the current 110 flows between the two electrodes 102a and 102b, a magnetic-field distribution having vertically opposite polarities is generated. Signals that are desired to be detected actually when the current 110 is caused to flow are slightly changing components of the current 110 (several % of the current 110 or smaller). Accordingly, if the magnetic field generated from the current 110 is detected directly, the gain of an amplifier (amplifier) cannot be increased, and those slight changes cannot be captured. As a method of cancelling the magnetic field generated from the current 110 itself, the coils 103a and 103b are placed at positions that are vertically equally distant from a line linking the two electrodes 102a and 102b. Changes in the magnetic field are individually detected by the coils 103a and 103b, and the adder 105 performs addition or subtraction on the changes. This makes it possible to cancel magnetic-field signals from current components (components to be DC components after detection) flowing through the entire living body, and it is possible to capture only minute magnetic-field changes caused by pulmonary or cardiac motions. Furthermore, since magnetic-field signals from current components flowing through the entire living body can be cancelled, it is possible to cancel out the influence of physical motions on the magnetic field, to measure only motions near the coils 103a and 103b, to thereby detect breathing or cardiac motions stably.

There are two methods of cancelling magnetic-field signals from current components flowing through the entire living body, and those two methods are explained separately about two cases. In a case where the two coils 103a and 103b are oriented in the same direction relative to the body surface (a case where the polarities of the coils are the same), the adder 105 performs an addition process of obtaining the sum of signals related to magnetic fields detected with the two coils. On the other hand, in a case where the two coils 103a and 103b are oriented in an opposite direction to each other relative to the body surface (a case where the polarities of the coils are different), the adder 105 performs a subtraction process of obtaining the difference of signals related to the magnetic field detected with the two coils. With these configurations, it is possible to cancel magnetic-field signals from current components flowing through the entire living body (components to be DC components after detection), and it is possible to capture only minute magnetic-field changes in the lungs or the heart at a high signal-detection sensitivity.

The two coils 103a and 103b are placed at vertically symmetric positions with respect to the line linking the two electrodes 102a and 102b.

The signal obtained through the addition or subtraction at the adder 105 is adjusted such that residual components can be cancelled at an amplitude/phase adjustment circuit 106 connected to the AC power supply 101, to which the two electrodes 102a and 102b are connected also. The adjusted signal is input from the adjustment circuit 106 to a cancel circuit 107 which performs cancellation or the like of residual components that are part of the magnetic-field signals from current components (components to be DC components after detection) flowing through the entire living body, and could not be cancelled completely at the adder 105. Then, after the residual components are minimized, synchronous detection is performed at a lock-in amplifier 108. In this manner, the residual components can be sufficiently cancelled from signals from the cancel circuit 107 before being input to the lock-in amplifier 108. Here, adjustment of the amplitude and phase by the adjustment circuit 106 can also be performed through performing AD (analog-digital) conversion on the signal obtained through the addition or subtraction at the adder 105 and performing automatic computation at a CPU, an FPGA or the like, and then automatically adjusting the signal to a signal having amplitude and a phase that are required for cancellation. In addition, regarding the amplitude and the phase required for cancellation, it is also possible to automatically perform calibration and setting on the adjustment circuit 106, after the electrodes 102a and 102b are placed on the living body and then a connection is established with a detection circuit 109 before respiratory measurement and cardiac-output measurement. At the lock-in amplifier 108, a measurement signal is compared with a reference signal, detection of a frequency component which is equal to each other between the measurement signal and the reference signal is performed, and a change in the impedance obtained from the two coils 103a and 103b is measured.

In order to measure the change in the impedance from an output voltage detected at the coil 103, the preamplifier 104, the adder 105, the cancel circuit 107 and the lock-in amplifier 108 constitute at least part of the detection circuit 109.

In addition, on the basis of known relationships between biological substances such as blood and intrapulmonary air, and biometric impedance (e.g. Yukihiro Sawada, and one other person, "Impedance plethysmography revisited," Japanese Journal of Physiological Psychology and Psychophysiology, vol 11, No. 2, 1993, 47-58), respiration ventilatory volumes and cardiac outputs can be calculated from outputs from the detection circuit 109.

Figure 4:
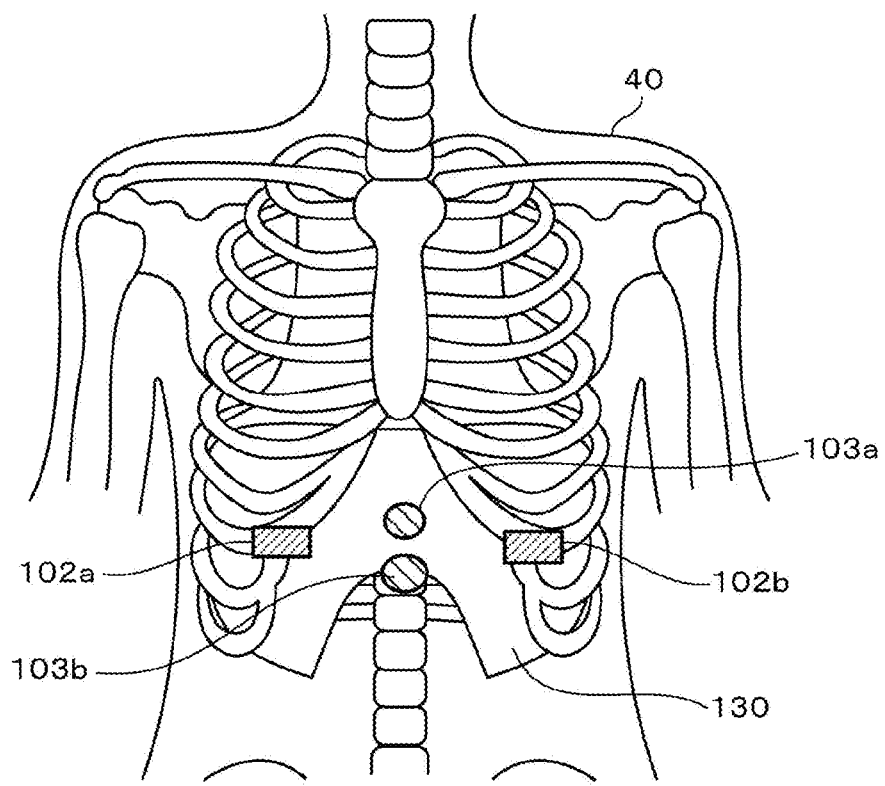
FIG. 4 is a figure illustrating placement positions of the electrodes and detection coils of the biological measurement apparatus of the first embodiment.

FIG. 4 is a figure illustrating a placement relationship among the two electrodes 102a and 102b, and the two coils 103a and 103b.

The two electrodes 102a and 102b are placed at the chest or abdomen so as to sandwich the sagittal plane of a living body 40. The two coils 103a and 103b are placed so as to sandwich the line linking the electrodes 102a and 102b, and detect voltages related to changes in the impedance of the living body accompanying motions of the living body 40. At least one coil of the two coils 103a and 103b is placed on a ventral body surface portion, which is directly above the range of motion in the diaphragm 130 inside the living body 40. Changes in the impedance accompanying motions of the lungs or the diaphragm in the respiratory activity of the living body 40 are detected by the two coils 103a and 103b, thereby measuring biosignals related to the respiratory activity.

Preferably, the electrodes 102a and 102b are placed directly above the position where the diaphragm moves up and down accompanying breathing. This is because the path of the current caused to flow by the two electrodes 102a and 102b presumably most noticeably changes due to intrapulmonary air that moves along with breathing.

In addition, preferably, the two electrodes 102a and 102b are placed at the chest or abdomen symmetrically about the sagittal plane of a living body 40. The two coils 103a and 103b are placed vertically symmetrically about the line linking the two electrodes 102a and 102b.

Figure 5:
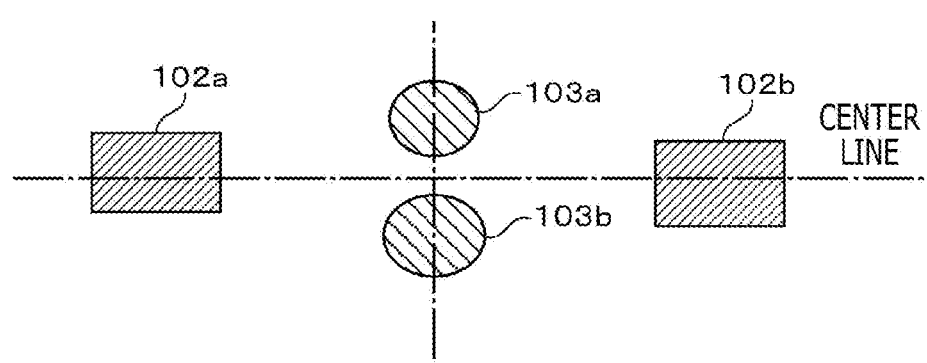
FIG. 5 is a figure illustrating the positional relationship among the electrodes and the detection coils of the biological measurement apparatus of the first embodiment.

FIG. 5 is a figure illustrating a placement relationship among the two electrodes 102a and 102b, and the two coils 103a and 103b in detail. As illustrated in FIG. 5, preferably, the two coils 103a and 103b are placed at vertically symmetric positions with respect to the center line of the electrodes 102a and 102b in order to cancel the influence of physical motions on the magnetic field generated by a current flowing between the two electrodes 102a and 102b. Accordingly, the two electrodes and the two coils are placed such that the line linking the two electrodes and the line linking the two coils cross at right angles at or near the center of the line linking the two coils. Note that the line linking the two electrodes and the line linking the two coils are only required to cross at substantially right angles.

Changes in the impedance of a subject include not only changes in the impedance brought about by expansion or shrinkage of the lungs or the diaphragm accompanying breathing of the subject or by changes in the intrapulmonary air, but also changes in the impedance brought about by physical motions not directly interrelated with breathing (e.g. motions of the hands of the subject) or by other factors.

Due to such changes in the impedance, the current 110 flowing between the two electrodes 102a and 102b changes, and the magnetic field generated by the current 110 also changes. Since each of the two coils 103a and 103b detects changes in the magnetic field brought about by changes in the current 110 as voltage changes, signals detected by each of the coils 103a and 103b might be influenced by physical motions not directly interrelated with breathing or by other factors.

Here, the inventors have found that in a case where measurement is performed when the electrodes 102a and 102b and the coils 103a and 103b have the placement relationship explained by using FIG. 4, the influence of physical motions such as motions of the hands of the subject, for example, is observed similarly in signals detected at the two coils 103a and 103b. Note that since the two coils 103a and 103b are placed nearby so as to be able to detect changes in the magnetic field brought about by changes in the high-frequency micro current 110 flowing between the two electrodes 102a and 102b, and additionally are placed symmetrically about the line linking the electrodes 102a and 102b, the influence of physical motions such as motions of the hands of the subject, for example, is presumably observed similarly in signals detected at the two coils 103a and 103b. Accordingly, the influence of physical motions can be reduced by obtaining the sum or difference of the signals detected at the two coils 103a and 103b depending on the polarities of the coils.

In addition, local changes occur in the current 110 due to changes in the impedance brought about by expansion or shrinkage of the lungs or the diaphragm accompanying breathing of the subject or changes in the intrapulmonary air, and changes in the magnetic field resulting from the local changes in the current 110 can be detected with the coils 103a and 103b. Thus, by detecting changes in the impedance accompanying motions of the lungs or the diaphragm in the respiratory activity of the living body 40 of the subject while reducing the influence of physical motions of the subject, biosignals related to the respiratory activity can be measured.

Figure 6A:
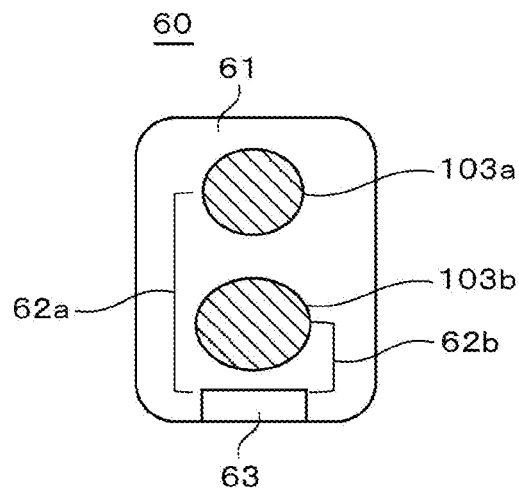
FIG. 6A is a top view of the detection coils used for the biological measurement apparatus of the first embodiment.
Figure 6B:
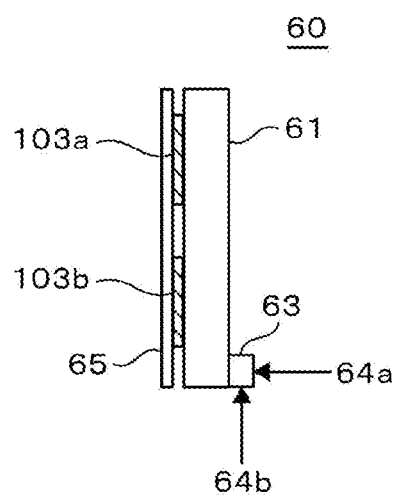
FIG. 6B is a side view illustrating the detection coils used for the biological measurement apparatus of the first embodiment.

FIG. 6A and FIG. 6B are figures illustrating the detection coils used for the biological measurement apparatus of the embodiment.

FIG. 6A illustrates a top surface portion of a quadrangular detection coil 60 on which the two coils 103a and 103b are formed integrally. Note that the detection coil 60 provided to the biological measurement apparatus has a holding section 61 that fixes the two coils 103a and 103b at a predetermined interval. The holding section 61 has rounded corners such that vertexes thereof are curved in order to ensure the safety of a living body. In addition, an auxiliary line (not illustrated) indicating the center line of the two coils 103a and 103b may be given such that the two coils 103a and 103b can be placed at positions symmetric about the line linking the two electrodes. Note that the detection coil 60 may be created with a flexible printed circuit (FPC). As illustrated in FIG. 6A, the detection coil 60 includes a connector 63 for connection with the detection circuit 109, a lead 62a that connects the coil 103a and the connector 63, and a lead 62b that connects the coil 103b and the connector 63.

FIG. 6B is a side view of the detection coil 60. An adhesive layer 65 is provided to the two coils 103a and 103b for pasting the detection coil 60 onto a living body. Thus, attachment to the living body becomes easy. In addition, the detection coil 60 may be disposal after use for sanitary reasons. A lead from the detection circuit 109 is connected to the connector 63 in the direction indicated by the arrow

64a for secure attachment to the detection coil 60. Note that the lead from the detection circuit 109 may be connected in the direction of the arrow 64b so as to avoid application of a load onto the living body.

Figure 7:
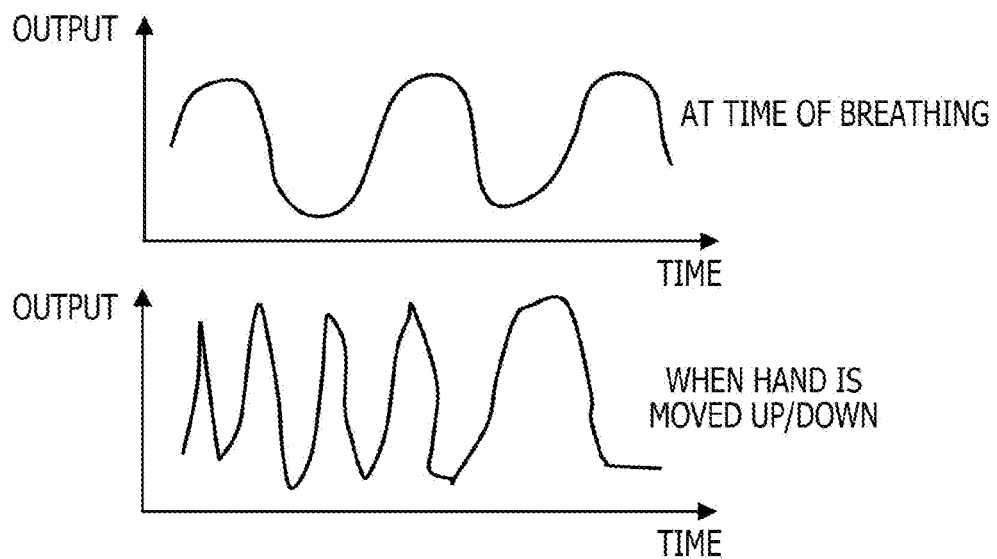
FIG. 7 is a figure illustrating waveforms detected by a detection circuit in a case where one coil is used.

FIG. 7 is a figure illustrating waveforms detected by a detection circuit in a case where one coil is used. The horizontal axis indicates time, and the vertical axis indicates an output of the detection circuit (e.g. impedance). The top graph in FIG. 7 represents a waveform detected at the time of breathing in a state where a subject is not moving, and the bottom graph in FIG. 7 represents a waveform detected when the subject stops breathing and moves his/her arm up and down. As illustrated in FIG. 7, if an arm is moved up and down, amplitude similar to that observed at the time of breathing is measured, and therefore, it is difficult to perform respiratory monitoring of general patients who are conscious and can talk or freely move their bodies, unlike unconscious serious ill patients.

Figure 8:
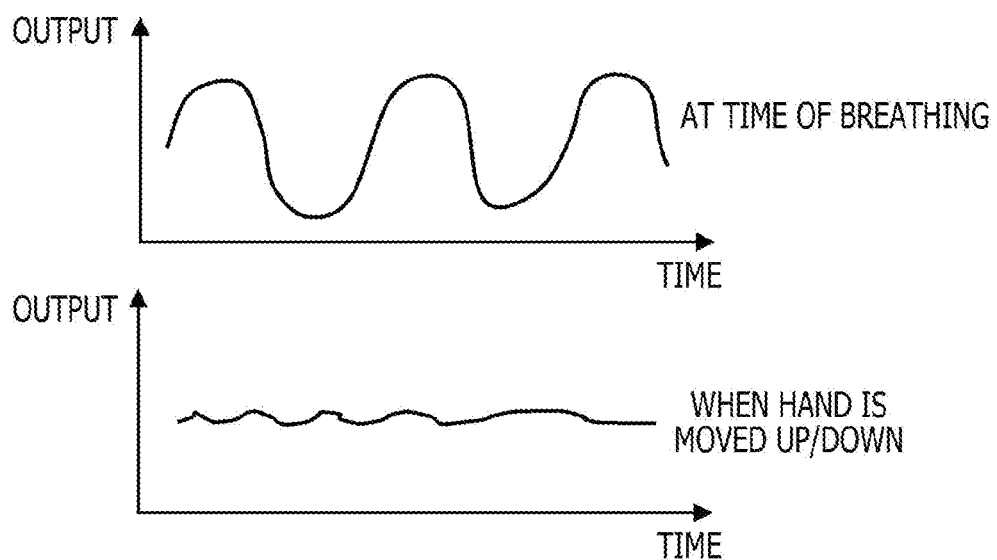
FIG. 8 is a figure illustrating waveforms detected by the biological measurement apparatus of the first embodiment.

FIG. 8 is a figure illustrating waveforms detected by the detection circuit 109 in a case where the two coils 103 described in the first embodiment are used. Similar to FIG. 7, the horizontal axis indicates time, and the vertical axis indicates an output of the detection circuit. Similar to FIG. 7, the top graph in FIG. 8 represents a waveform detected at the time of breathing in a state where a subject is not moving, and the bottom graph in FIG. 8 represents a waveform detected when the subject stops breathing and moves an arm of the user up and down. As illustrated in the top graph in FIG. 8, it can be known that respiratory monitoring performed in a state where the subject is not moving is possible. Note that in the one example of the top graph in FIG. 8, the output value increases when the subject makes an expiratory motion, and decreases when the subject makes an inspiratory motion, for example. For example, in regular respiratory motions, regular peaks and troughs are observed in the output signal. In this manner, the respiratory rate, the depth of breathing, the rhythm of breathing and the like can be measured based on the waveforms of output signals, and respiratory monitoring is possible.

On the other hand, in the bottom graph in FIG. 8, large changes in the output signal are not observed unlike the bottom graph in FIG. 7. This indicates that the influence of the motion of moving the arm up and down is cancelled out (reduced) because the adder 105 performs addition or subtraction of output voltages of the two coils 103. Thus, as illustrated in the top graph in FIG. 8, changes in the impedance accompanying breathing can be measured accurately.

As has been explained above, according to the first embodiment, respiratory monitoring also capable of measuring the ventilatory volume or the like of breathing can be performed on general patients like those who are in general wards or receiving in-home care, or who can walk.

Second Embodiment

A biological measurement apparatus that measures cardiac outputs is explained in a second embodiment.

Figure 9A:
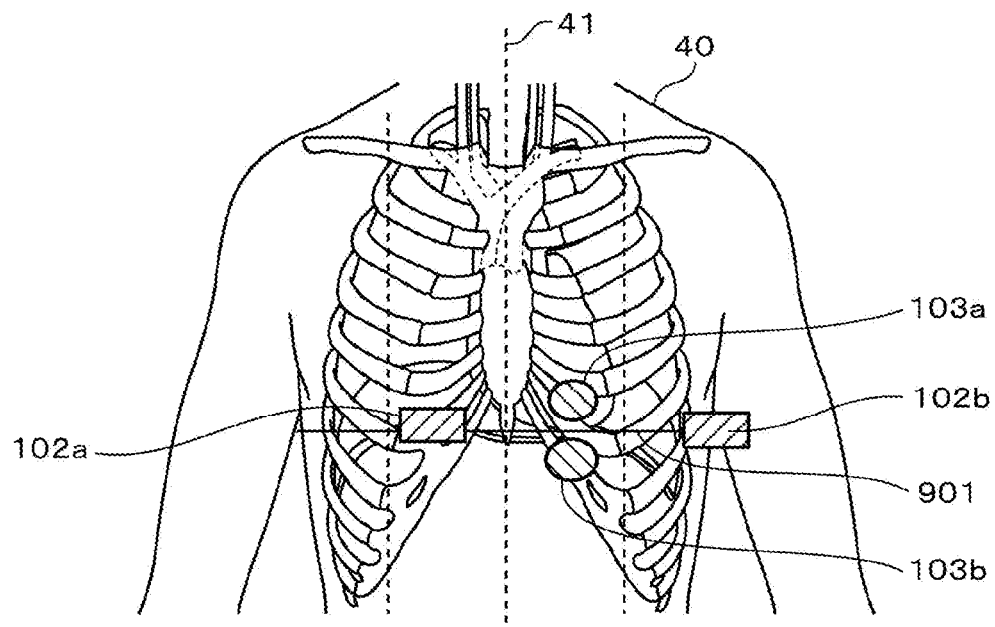
FIG. 9A is a figure for explaining cardiac-output measurement performed by using a biological measurement apparatus of a second embodiment.
Figure 9B:
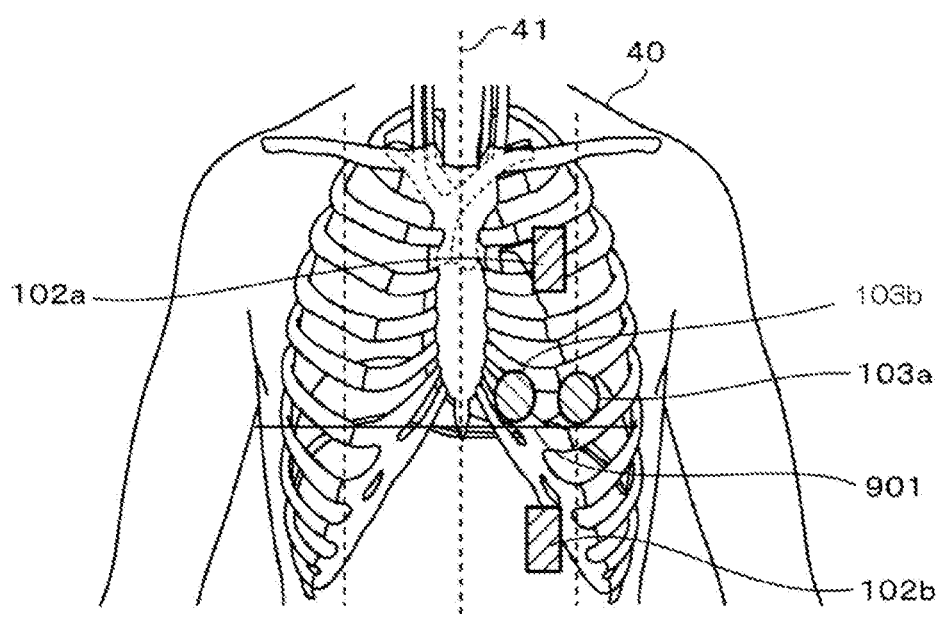
FIG. 9B is a figure for explaining cardiac-output measurement perform by another method by using the biological measurement apparatus of the second embodiment.

FIGS. 9A and 9B are figures illustrating placement positions of the two electrodes 102 and the two coils 103 of the biological measurement apparatus of the second embodiment on a subject.

As illustrated in FIG. 9A, the two electrodes 102a and 102b are placed such that the line linking the two electrodes 102a and 102b passes directly above an apex 901 and becomes perpendicular (or substantially perpendicular) to a body axis 41 of the living body 40. Here, the apex 901 may include an area of and near the apex of the heart of the subject, that is, the vicinity of the apex, and this applies also to the following explanation. Then, the two coils 103a and 103b are placed vertically symmetric about the center of the line linking the two electrodes 102a and 102b, and the line linking the two coils 103a and 103b becomes parallel (or substantially parallel) to the body axis 41 of the living body 40. Thus, motions of the left ventricle that sends blood out to the whole body by contraction of the left ventricle can be observed. That is, by detecting, by the two coils 103a and 103b, changes in the impedance accompanying cardiac motions of the living body, biosignals such as cardiac outputs related to the cardiac motions are measured.

The two electrodes 102a and 102b are only required to be placed such that at least a partial area of an area between the electrodes is positioned directly above the heart inside the living body, more preferably, positioned directly above the apex 901 of the heart. The two coils 103a and 103b are only required to be placed such that at least a partial area of an area between the coils is positioned directly above the heart inside the living body, more preferably, positioned directly above the apex 901 of the heart.

In FIG. 9B, the two electrodes 102a and 102b are placed such that the line linking the two electrodes 102a and 102b passes directly above the apex 901 and becomes parallel (or substantially parallel) to the body axis 41 of the living body 40. Then, the two coils 103a and 103b are placed so as to be horizontally symmetric about the center of the line linking the two electrodes 102a and 102b, and placed such that the line linking the two coils 103a and 103b becomes perpendicular (or substantially perpendicular) to the body axis 41 of the living body 40. Thus, motions of the left ventricle that sends blood out to the whole body by contraction of the left ventricle can be observed. That is, by detecting, by the two coils 103a and 103b, changes in the impedance accompanying cardiac motions of the living body, biosignals such as cardiac outputs related to the cardiac motions are measured.

The two electrodes 102a and 102b are only required to be placed such that at least a partial area of an area between the electrodes is positioned directly above the heart inside the living body, more preferably, positioned directly above the apex 901 of the heart. The two coils 103a and 103b are only required to be placed such that at least a partial area of an area between the coils is positioned directly above the heart inside the living body, more preferably, positioned directly above the apex 901 of the heart.

Figure 10:
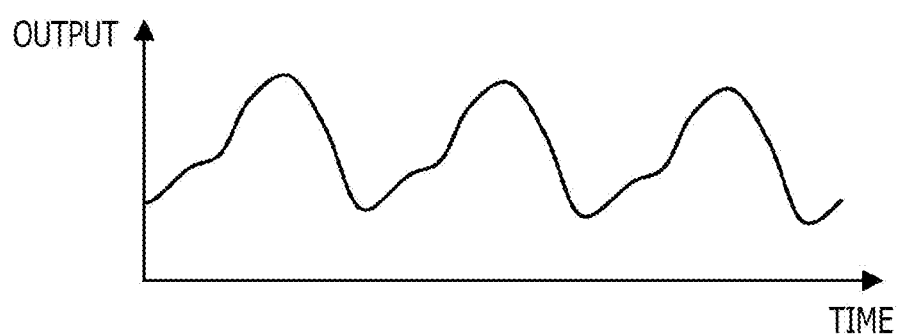
FIG. 10 is a figure illustrating a measurement result of a cardiac output measured by using the biological measurement apparatus of the second embodiment.

FIG. 10 is a figure of a waveform obtained by detecting a cardiac output with the biological measurement apparatus. The horizontal axis indicates time, and the vertical axis indicates an output of the detection circuit 109. The cardiac output can be computed from the height and area of the waveform illustrated in FIG. 10. The detection circuit 109 can output a signal related to the cardiac output of the living body 40 on the basis of signals related to a magnetic field detected with the two coils 103a and 103b. In addition, an abnormality of the heart, for example, an abnormality of a valve, a ventricle or the like, can be estimated from the shape of the waveform.

According to the second embodiment explained thus far, accurate cardiac-output measurement can be performed on general patients who can talk or move their bodies while the measurement is being performed.

As explained in the first embodiment and the second embodiment, one aspect of the biological measurement apparatus includes: the at least two electrodes 102a and 102b that are attached to a living body; the power supply 101 that causes an AC current to flow between the two electrodes; the at least two coils 103a and 103b that are placed so as to sandwich the line linking the two electrodes, and detect a magnetic field related to a change in the AC current accompanying a change in the impedance of the living body; and the detection circuit that performs addition or subtraction of signals related to the magnetic field detected with the two coils 103a and 103b, and outputs the signals as a change in the impedance. Here, for example, a plurality of the detection coil 60 each including the two coils 103a and 103b may be placed between the two electrodes 102a and 102b to perform measurement, and it is only required that there are at least two coils 103a and 103b. Similarly, it is only required that there are also at least two electrodes 102a and 102b. In addition, the signals related to the magnetic field detected with the two coils 103a and 103b may be signals obtained through signal processing such as signals obtained by amplifying signals (specifically, voltages) detected with the two coils by the preamplifier 104, or may be those detected signals. The detection circuit may perform the process of addition or subtraction of signals related to the magnetic field detected with the two coils 103a and 103b, by switching the process between addition and subtraction by user operation or the like, or the detection circuit may perform the process of only either one of addition and subtraction.

What is claimed is:

1. A biological measurement method comprising:
   attaching at least two electrodes to a patient;
   sending, via a power supply, an AC current to flow between the at least two electrodes;
   placing on the patient, at least two coils so as to sandwich a line linking the at least two electrodes, and detecting a magnetic field related to a change in the AC current, the change accompanying a change in impedance of the patient; and
   performing, via a detection circuit, an addition process to add together or a subtraction process to take the difference between signals related to the magnetic field detected with the at least two coils, and outputting the signals as the change in the impedance,
   wherein the at least two electrodes are symmetrically positioned on a chest or an abdomen of the patient with respect to a sagittal plane of the patient, and
   the at least two coils are arranged symmetrically with respect to the line linking the at least two electrodes.
2. The biological measurement method according to claim 1, wherein
   placing at least one coil of the at least two coils at a ventral body surface directly above a range of motion of a diaphragm inside the patient, and
   detecting, by the at least two coils, a change in the impedance caused by a motion of a lung or the diaphragm in a respiratory activity of the patient, based on the signals related to the magnetic field detected, and
   measuring a biosignal related to the respiratory activity.
3. The biological measurement method apparatus according to claim 2, wherein
   placing the at least two coils vertically symmetrically about the line linking the two electrodes.
4. The biological measurement method according to claim 1, wherein
   placing the at least two electrodes such that at least a partial area between the at least two electrodes is positioned directly above a heart inside the patient,
   placing the at least two coils such that at least a partial area between the at least two coils is positioned directly above the heart inside the patient, and
   detecting by the at least two coils, a change in the impedance, the change caused by a cardiac motion of the patient, based on the signals related to the magnetic field detected, and
   measuring a biosignal related to the cardiac motion.
5. The biological measurement method according to claim 4, wherein
   placing the at least two electrodes such that at least a partial area between the at least two electrodes is positioned directly above an apex of the heart.
6. The biological measurement method according to claim 4, wherein
   placing the at least two coils such that at least a partial area between the at least two coils is positioned directly above an apex of the heart.
7. The biological measurement method according to claim 4, wherein,
   on a basis of the signals related to the magnetic field detected with the at least two coils, outputting, via the detection circuit, a signal related to a cardiac output of the patient.
8. The biological measurement method according to claim 1, wherein
   placing the at least two electrodes such that the line linking the at least two electrodes becomes perpendicular to a body axis of the patient, and
   placing the at least two coils such that a line linking the at least two coils becomes parallel to the body axis of the patient.
9. The biological measurement method according to claim 1, wherein
   placing the at least two electrodes such that the line linking the at least two electrodes becomes parallel to a body axis of the patient, and
   placing the at least two coils such that a line linking the at least two coils becomes perpendicular to the body axis of the patient.
10. The biological measurement method according to claim 1, wherein
    placing the at least two electrodes and the at least two coils such that the line linking the at least two electrodes and a line linking the at least two coils cross at right angles.
11. The biological measurement method according to claim 1, further comprising:
    fixing, via a holding section, the at least two coils at a predetermined interval.
12. The biological measurement method according to claim 1, wherein
    placing the at least two coils such that directions of the at least two coils relative to a body surface become a same direction, and
    performing, via the detection circuit, the addition process of obtaining a sum of the signals related to the magnetic field detected with the at least two coils.
13. The biological measurement method according to claim 1, wherein
    placing the at least two coils such that directions of the at least two coils relative to a body surface become opposite directions, and
    performing, via the detection circuit, the subtraction process of obtaining a difference of the signals related to the magnetic field detected with the at least two coils.

* * * * *